United States Patent [19]

Haakana

[11] Patent Number: 4,869,098

[45] Date of Patent: Sep. 26, 1989

[54] DEVICE AND METHOD FOR ANALYZING THE ELASTIC AND/OR VISCOUS PROPERTIES OF GELS OR LIQUIDS

[75] Inventor: Markku Haakana, Bollnäs, Sweden

[73] Assignee: Ermartic International AB, Bollnas, Sweden

[21] Appl. No.: 246,398

[22] PCT Filed: Jan. 8, 1988

[86] PCT No.: PCT/SE88/00001

§ 371 Date: Sep. 8, 1988

§ 102(e) Date: Sep. 8, 1988

[87] PCT Pub. No.: WO88/05165

PCT Pub. Date: Jul. 14, 1988

[51] Int. Cl.⁴ .......................................... G01N 11/10
[52] U.S. Cl. .......................................... 73/64.1; 73/59
[58] Field of Search .................................. 73/64.1, 59

[56] References Cited

U.S. PATENT DOCUMENTS 4,542,645  9/1985  Richardson et al. ................. 73/64.1

*Primary Examiner*—Tom Noland
*Assistant Examiner*—Joseph W. Roskos
*Attorney, Agent, or Firm*—Charles E. Brown; Charles A. Brown

[57] ABSTRACT

A device and a method for analyzing the elastic and/or viscous properties of gels or liquid is presented. The device has a member which moves reciprocally when driven by an electrical motor. A sensing member is provided which contacts the gel or liquid to analyze the properties of the gel or liquid. The sensor member is pivotably connected to the movable member through a connection, which on one hand puts the sensing member in motion upon movement of the movable member; but also allows relative movement of the sensing member and the movable member with respect to each other. A sensor apparatus is provided for delivering information pertaining to the resistance exerted by the gel or liquid on the sensing member upon movement of the movable member. A control unit, timer and switch are used to provide variable adjustment of the distance the electrical motor moves the movable member during the analysis process. The method is based upon movement of the sensing member to compress the gel or liquid between itself and a liquid movement delimiting wall.

12 Claims, 2 Drawing Sheets

DEVICE AND METHOD FOR ANALYZING THE ELASTIC AND/OR VISCOUS PROPERTIES OF GELS OR LIQUIDS

TECHNICAL FIELD OF THE INVENTION

The present invention relates to a device for analysing the elastic and/or viscous properties of gels or liquids according to the preamble of the appended claim 1.

PRIOR ART

A device of the type defined above is described in the Swedish patent application No. 8205627-6. Although this prior device has led to a substantial improvement concerning the possibilities to analyse the elastic and/or viscous properties of gels or liquids, it has however turned out that its analysing accuracy occasionally is not as good as desired. Other known analysis devices, which are based on different construction principles, have to an even greater extent the same drawback. As an example reference can be made to the device according to the Swedish patent application No. 8104453-9. In this device a movable member is displaced or tipped and the analysis result is based on measurement of the movement which a certain force gives rise to or measurement of the resistance of the liquid against a certain predetermined displacement of the movable member. In the German patent publication No. 2909087 a device is described which is based on the fact that a measuring body is forced to move into, through and subsequently out of a liquid, while the resistance against this movement is measured. In practice the measuring body describes a curved path through the liquid to be analysed.

OBJECT OF THE INVENTION

The object of the present invention is to provide a device, by means of which it has to be possible to obtain very good measurement results with an extraordinary reproduceability so far as the elastic and/or viscous properties of gels and liquids are concerned. In particular it is an object to design the device so that it may be adapted to the gels or liquids to be analysed as well as the demands made upon the analysis results. Depending on the character of the process in which the device is going to be utilized, it is possible that the elastic properties may be more interesting than the viscous ones or conversely.

SUMMARY OF THE INVENTION

The object of the invention is primarily obtained by the embodiment which gives rise to a very simple construction, which imply a maximum of sensitivity of the sensing member and by that a maximum of measuring sensitivity. When the sensing member is moved through the liquid the resistance exerted by the liquid will be directly transmitted to the flexible portion and cause bending thereof and accordingly an output signal typical for the resistance from the sensor, without possible jamming in hinge arrangements and the like leading to a risk of some doubtful measuring results. Thus, the flexible portion will act as a pivot center for the pivoting of the sensing member during the analysis process. For the rest the flexible portion allows the sensing member to act as a flexible member, so that the real movement of the sensing member varies in dependence of the viscosity of the liquid.

It is very important for the attainment of an excellent analysis result that an accurate adjustment of the distance, by which the driving means moves the movable member during the analysis process, may be carried out in dependence of the character of the gel or liquid to be analysed and in dependence of for what purpose the analysis results shall be used. For example in viscosity measurements concerning comparatively thin fluid liquids it has turned out to be suitable to use a comparatively long movement distance. In the application of the device to analysing comparatively viscous gels and liquids it has turned out that substantially improved analysis results are obtained by comparatively short distances of movement. This is in particular the case if the elastic properties of the gel or liquid are of proportionately great importance in comparison with the purely viscous properties. In the application of the invention within cheese production in order to determine the rigidity of a cheese coagulant and by that a point at which the coagulation is to be terminated, there is a desire to continuously observe the coagulation process in order to obtain information about the exact time for the termination of the coagulation. On such an application it is very important that the analysis device does not interfere with the coagulation process. It has surprisingly been discovered that it is possible to achieve extraordinarily reliable analysis results by means of the device according to the invention already at so extremely short distances of movement that the coagulation process may proceed substantially undisturbed, and this in spite of the analysis process having to be repeated several times during the coagulation process. Furthermore, by utilizing proportionately short distances of movement the measuring result is getting typical to a greater extent for the elastic properties of the gel or the liquid, which has turned out to be particularly essential in cheese coagulents. It has namely turned out that already at a distance of movement being comparatively short after all, a disturbance desolating to the measuring result occurs. Thus, by means of the device according to the invention it is possible to empirically make clear which distance of movement leads to the correct, desired analysis result in each actual case. Thus, the device may subsequently easily and rapidly be readjusted for use with gels or liquids with varying properties, which is essential since a given process equipment usually is utilized for processes with gels or liquids with at least in some degree varying properties.

Furthermore, the invention relates to a method for determination of primarily elastic properties of a gel or liquid, especially the coagulation state of cheese pulp. The characteristics of this method appear more exactly from the appended claims.

BRIEF DESCRIPTION OF THE DRAWINGS

With reference to the appended drawings below follows a specific description of an embodiment of the invention cited as an example.

In the drawings.

DETAILED DESCRIPTION OF PREFERRED EMBODIMENTS OF THE INVENTION

In the following a device according to the invention will primarily be described as adapted to the cheese producing technique for determining when the coagulation of cheese pulp shall be terminated. However, it should be understood that the device may be used for determination of the elastic and/or viscous properties of any gels or liquids. By the expression "elastic and/or viscous properties" all properties related to the viscosity of gels or liquids are intended to be comprised. As an example of gels or liquids creams, salves and pastes for body and health care, fats, oils, coating and isolation compositions, paints, lacquers, as well as food products, as gels, soups, creams, jams etc. may be mentioned.

Figure 1:
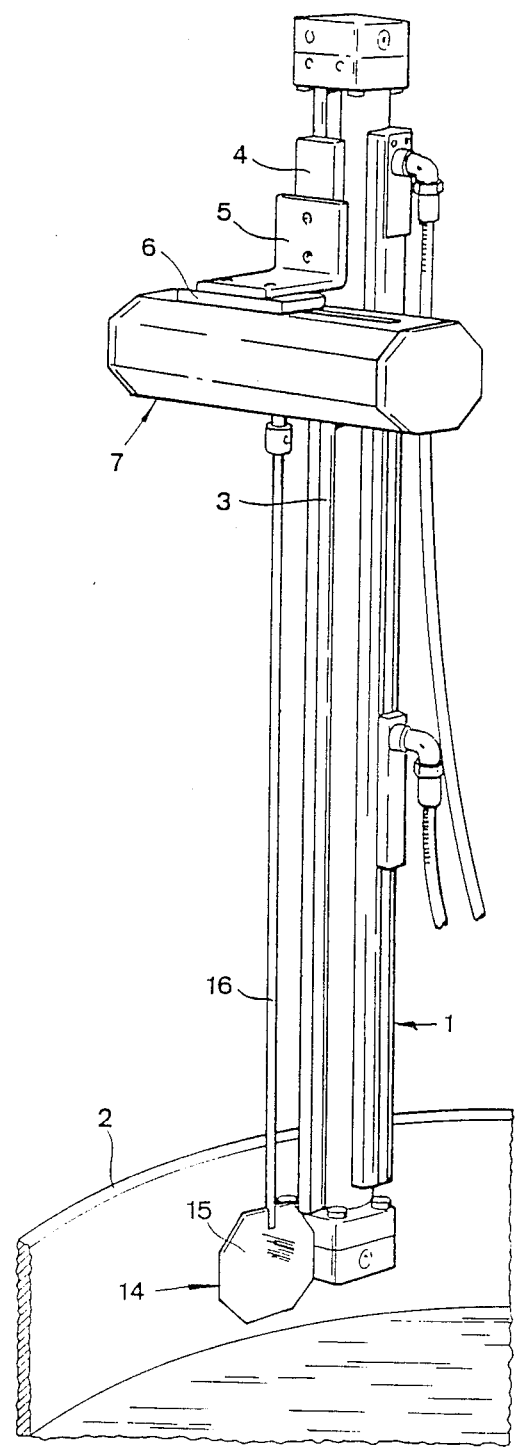
FIG. 1 is a perspective view which schematically illustrates the analysis device, a part of a process vessel being indicated.

As appears from FIG. 1 the device comprises a support member 1 adapted to be supported in a position above a partly indicated process vessel 2 by means of supporting components not shown. The support member 1 has the character of a cylinder, in which a piston is movable to and fro. The cylinder 1 is in the example of so called origa-type and has a longitudinal slit 3, through which a bracket 4 projects, which is connected to the piston.

One of the legs of an angle element 5 is attached to this bracket 4. The other leg of the angle element is attached to a support plate 6, which carries a movable member 7 formed as a casing. More exactly the movability of the movable member 7 is obtained by a driving means 8 shown in FIG. 2. The movable member 7 is controlled to perform a reciprocating rectilinear motion. The driving means 8 has in the example the character of a linear electrical motor of a type well-known per se. The motor has a first part 9, which is attached to the plate 6 through a portion 10, which projects through the casing of the movable member 7 through a slit 11. A second part 12 of the motor is fixed within the member 7. When the motor 8 is provided with electrical current the parts 9 and 12 will move with respect to each other so that the member 7 moves along the double arrow 13.

Figure 2:
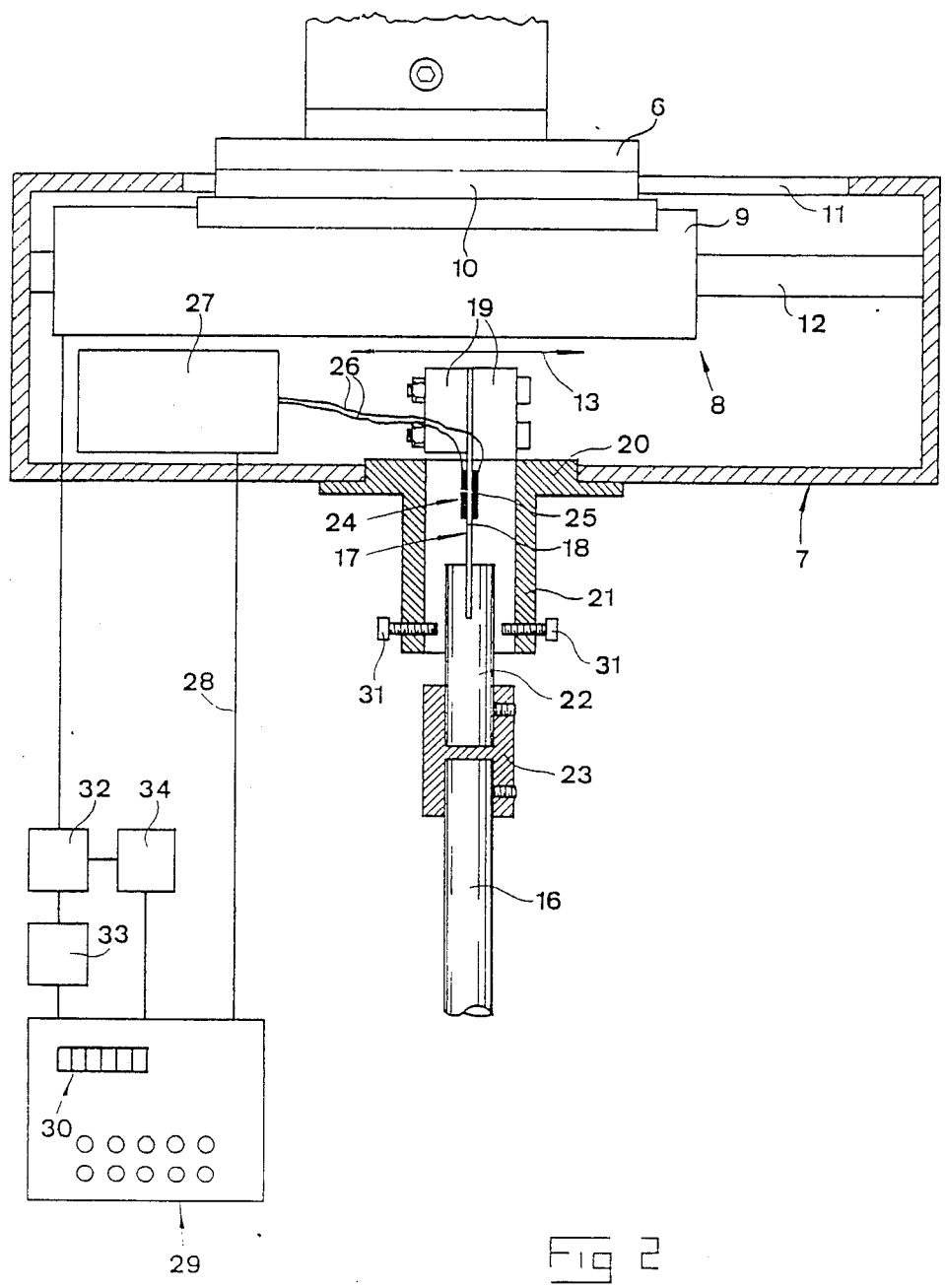
FIG. 2 is a view which with some schematical additions shows a part of the device according to FIG. 1 in an enlarged scale and in a sectioned view.

The device comprises a generally by 14 denoted sensing member, which in the example has a plate 15 intended for contact with a gel or liquid, the properties of which are to be analysed, by immersing into this. The sensing member has also a shaft 16 and is connected to the movable member 7 through a connection 17, which on one hand tends to put the sensing member 14 in motion upon movement of the movable member 7 but on the other allows some relative movement of the sensing member and the movable member with respect to each other. The connection 17 comprises a flexible portion 18, which has the character of a plate spring. The upper portion of this is releasable clamped between two parts 19, one of which is attached to the member 7. The other part 19 may be loosened for exchange of the plate spring 18. It is preferred that the right part 19 in FIG. 2 is attached to an element 20, which in its turn is releasably attached to the casing part of the member 7 and furthermore has a sleeve 21, inside of which the plate spring 18 is at least partially located. The end of the plate spring 18 turned away from the parts 19 may be secured to a connection member 22, which in its turn is releasably attached to a coupling member 23, which releasably receives also the shaft 16 of the sensing member 14.

The device comprises a sensor apparatus 24 for delivering information concerning the resistance exerted by the gel or liquid on the sensing member 14 upon movement of the member 7. The sensor apparatus is arranged to deliver information typical for the bending state of the flexible portion 18. More exactly the sensor apparatus 24 has the character of a strain sensor or tension meter comprising a flexible portion 18 and elements 25 arranged thereon, which react upon the bending state of the portion 18 by delivering an electrical signal being related thereto. The element 25 comprises one or more wires which are more or less stretched in dependence of the bending of the portion 18 and by that get a varying resistance value. Cables 26 connect the electrical circuit formed by the elements 25 with an amplifier 27, which in its turn through a cable 28 delivers a piece of information typical for the bending state of the portion 18 to a unit 29, which is provided with means for visually or in another arbitrary way indicate the information.

As it appears from FIG. 2 means 31, e.g. screws, are co-ordinated with the sleeve 21 in order to delimit the bending of the portion 18 permitted. Accordingly, the means 31 are intended to be adjusted so that they only start to act bending limiting if the sensing member is subjected to a greater resistance than normally expected.

The unit 29 has suitably also the character of a control unit and may consist of a computer. The device comprises means for variable adjustment of the distance that the motor 8 moves the movable member 7 during the analysis process. The distance desired is suitably adjustable by means of the keyboard of the control unit 29.

According to a first embodiment of the device the motor 8 may be arranged to cause a movement of the member 7 with a constant speed. The current supply to the motor 8 is regulated by means of a regulating member 32 designed as a switch. A further regulating member 33 is adjustable by means of the unit 29 and has a character of a timer, since it determines the time for the movement of the member 7. The timer 33 receives this time through a connection from the control unit 29.

According to a further embodiment the device may also comprise means for variable adjustment of the speed, by which the motor 8 moves the movable member 7 during the analysis process. This adjusting means is indicated at 34 in FIG. 2. The speed desired is given to the adjusting means 34 through a connection to the control unit 29 and the adjusting means 34 is for instance connected to the regulating member 32, so that the latter is controlled to perform the current supply to the motor 8 in such a way that the desired speed of movement is obtained.

When the device shall be used for analysing the properties of a certain gel or liquid the starting parameters are first of all set on the basis of experience, i.e. the design and size of the sensing member 14 as far as it concerns the part to be immersed into a gel or liquid, suitable place with respect to the vessel, where the analysis shall be carried out, as well as speed and distance of the movement of the member 7. After that an experimental phase is started, in which it is proved if the analysis results are correct and possible correction of the variables above is carried out. The sensing member will of course follow the movement of the member 7 during the analysis process and the resistance exerted by the gel or liquid on the sensing member then gives rise to a certain resistance, which results in a bending of the flexible portion 18 and a value typical for this bending is obtained by the indicating equipment 30. It should be understood that the sensing member 15 due to the flexibility of the portion 18 will move somewhat less in the gel or liquid than the movable member 7. It has been found to be suitable to design the device so that the distance of motion of the member 7 may be varied between 0 and 50 mm. Very short distances of movement of the movable member 7, e.g. distances between 1 and 10 mm, are chosen when the gels or liquids are very sensitive to influences from the outside, which, for example if the movements were too great, could cause disturbance of the stability of the gel or liquid. It is preferred that the measuring values only are registered during the movement of the member 7 in one direction and accordingly not during the return motion. The measuring values may of course be continuously registered during the complete motion or only the highest measuring value during the motion may be chosen.

In particular in connection with gels and liquids with comparatively great rigidity and viscosity and especially also low stability, it has turned out to be suitable to choose proportionately short distances of movement. An example thereof is constituted by the analysis of coagulating cheese pulp. In this application it has turned out to be suitable to choose a distance of movement lying between 1 and 30 mm, preferably between 3 and 10 mm. Such a very short distance of movement of the member 7, which gives rise to an even shorter distance of movement of the sensing member 14 itself, i.e. its plate 15, does primarily indicate what the elastic properties of the cheese pulp are. It has been found that it is primarily these elastic properties which are typical for the point of time at which the cheese pulp shall be broken and accordingly the coagulation shall be influenced to stop. In order to clarify in particular the elasticity properties to an even greater extent it has turned out to be suitable to locate the device according to the invention and a vessel containing the cheese pulp so with respect to each other that the sensing member tends to compress the cheese pulp between itself and a delimiting wall (see for instance the wall of the vessel 2 in FIG. 1) upon movement of the movable member 7, said wall being at a distance not greater than 50 cm, preferably a distance between 10 and 30 cm, most preferably a distance between 15 and 20 cm, from the sensing plate 15 of the sensing member during the analysis process. The cheese pulp located between the vessel wall and the sensing plate 15 will by that be subjected to very small shearing loads, and accordingly the viscous properties of the cheese pulp will influence the analysis result to a proportionately small extent. It has turned out that the short distances of movement discussed above constitute a disturbance of the coagulation process of the cheese pulp negligible in this connection, which accordingly means that it is possible to monitor the whole coagulation process without moving the sensing member to other places in the cheese pulp. Such moving would itself through the introduction of the sensing member on a new place constitute a disturbance which in a late phase of the coagulation process would be unacceptable in many cases. In the application of the device in connection with cheese pulp it has turned out to be suitable to design the sensing body 15 of the sensing member immersed into the cheese pulp so that it has a surface facing in its direction of movement, said surface being between 1,000 and 100,000 mm², preferably between 5,000 and 20,000 mm². Very good analysis results have been achieved by a surface of about 1 dm².

In sensible gels and liquid systems the motion speed of the member 7 is of course chosen so low that the sensing member disturbs the stability of the gel or liquid in a very small degree. In a corresponding way the sensing member is immersed into the gel or liquid by fluid supply to the cylinder 1 so slowly that improper disturbance of the gel or liquid does not occur.

Naturally the device may be modified in several ways within the scope of invention.

I claim:
1. A device for analysing the elastic and/or viscous properties of gels or liquids, said device comprising a movable member (7), driving means (8) for moving said movable member (7) in a reciprocating motion, a sensing member (14) being pivotably connected to said movable member (7), said sensing member (14) being positioned to contact a gel or liquid of which the properties thereof are to be analysed, said movable member (7) being pivotably connected to said sensing member (14) by a connector (17) whereby said sensing member (14) moves in motion upon movement of said movable member (7) and also allows relative movement of said sensing member (14) and said movable member (7) with respect to each other, and a sensor apparatus (24) for determining information representative of the resistance exerted by the gel or liquid on said sensing member (14) upon movement of said movable member (7), said connection (17) including a flexible portion (18) which is bendable in response to movement of said sensing member (14) contacting the gel or liquid whereby resistance information is generated, said sensor apparatus (24) comprising a sensor (25) coordinated with said flexible portion (18) for receiving the resistance information.

2. The device according to claim 1, wherein said device further comprises means (29,32,33) for variable adjustment of the distance said driving means (8) moves said movable member (7) during the analysis of the gel or liquid.

3. The device according to claim 1, wherein said device further comprises means (29,32,34) for variable adjustment of the speed by which said driving means (8) moves said movable member (7) during the analysis of the gel or liquid.

4. The device according to claim 2, wherein said device further comprises means (29,32,34) for variable adjustment of the speed by which said driving means (8) moves said movable member (7) during the analysis of the gel or liquid.

5. The device according to claim 1, wherein said movable member (7) is controlled to perform a substantially rectilinear and substantially horizontal movement.

6. The device according to claim 1, wherein said device includes means (33) for adjusting the distance of motion of said movable member (7), and said adjusting means (33) determines the duration of the movement.

7. The device according to claim 1, wherein said driving means (8) is adapted to move said movable member (7) with constant speed.

8. The device according to claim 1, wherein said sensor (25) is a strain sensor.

9. A device for analysing the elastic properties of a gel-like liquid, especially for analyzing the coagulation state of cheese, said device comprising a movable member (7), driving means (8) for moving said movable member (7), said movable member being controlled to perform a substantially rectilinear and horizontal reciprocating motion, a sensing member (14) being positioned to contact the gel-like liquid of which the properties thereof are to be analysed, said sensing member (14) being pivotably connected to said movable member (7) through a connection (17), said connection (17) on one hand permitting horizontal motion of said sensing member (17) upon movement of said movable member (7) and also allowing relative movement of said sensing member (14) and said movable member (7) with respect to each other, and a sensor apparatus (24) for determining information representative of the resistance of the gel-like liquid on said sensing member (14) upon movement of said movable member (7), a wall of a vessel for delimiting liquid motion, said delimiting vessel wall and said sensing member (14) being located with respect to each other whereby said sensing member (14) horizontally compresses the gel-like liquid against said delimiting vessel wall upon movement of said movable member (7), said delimiting vessel wall being at a distance not greater than 50 cm, preferably the distance between 10 and 30 cm, from said sensing member (7) during the analysis of the gel-like liquid.

10. The device according to claim 9, wherein said movable member (7) is moved between 1 and 30 mm, preferably between 3 and 10 mm, in the direction towards said delimiting vessel wall during the analysis of the gel-like liquid.

11. The device according to claim 9, wherein said sensing member (14) has a surface facing in its direction of movement, and the area of said surface facing is between 1,000 and 10,000 mm$^2$, preferably between 5000 and 20000 mm$^2$.

12. The device according to claim 10, wherein said sensing member (14) has a surface facing in its direction of movement, and the area of said surface facing is between 1,000 and 10,000 mm$^2$, preferably between 5,000 and 20,000 mm$^2$.

* * * * *